(12) United States Patent
Uchida et al.

(10) Patent No.: US 7,288,766 B2
(45) Date of Patent: Oct. 30, 2007

(54) INFRARED GAS DETECTOR AND METHOD OF THE SAME

(75) Inventors: Kouji Uchida, Kariya (JP); Takahiko Yoshida, Okazaki (JP)

(73) Assignee: DENSO CORPORATION, Kariya (JP)

( * ) Notice: Subject to any disclaimer, the term of this patent is extended or adjusted under 35 U.S.C. 154(b) by 187 days.

(21) Appl. No.: 11/095,468

(22) Filed: Apr. 1, 2005

(65) Prior Publication Data
US 2005/0218327 A1   Oct. 6, 2005

(30) Foreign Application Priority Data
Apr. 1, 2004   (JP)   ............... 2004-109379

(51) Int. Cl.
*G01N 21/00* (2006.01)
(52) U.S. Cl. ............... 250/338.5; 250/339.01
(58) Field of Classification Search ........... 250/339.12, 250/339.13, 338.5, 339.01
See application file for complete search history.

(56) References Cited

U.S. PATENT DOCUMENTS

| 3,790,798 | A | * | 2/1974 | Sternberg et al. ........... 250/345 |
| 4,355,233 | A | * | 10/1982 | Warnke et al. ............... 250/345 |
| 5,041,723 | A | * | 8/1991 | Ishida et al. ............ 250/339.01 |
| 5,418,366 | A | * | 5/1995 | Rubin et al. ................. 250/343 |
| 5,468,961 | A | * | 11/1995 | Gradon et al. ............... 250/343 |
| 5,591,975 | A | * | 1/1997 | Jack et al. ................ 250/338.5 |
| 5,886,348 | A | * | 3/1999 | Lessure et al. ......... 250/339.13 |
| 2002/0026822 | A1 | * | 3/2002 | Reading et al. ............. 73/31.05 |

FOREIGN PATENT DOCUMENTS

JP   A-2003-50203   2/2003

* cited by examiner

*Primary Examiner*—David Porta
*Assistant Examiner*—Casey Bryant
(74) *Attorney, Agent, or Firm*—Posz Law Group, PLC

(57) ABSTRACT

An infrared gas detector for detecting a density of a sample gas includes an infrared light sensor for detecting the density of the sample gas under an influence of water vapor based on an intensity of received infrared light of a specific wavelength, and a humidity sensor for detecting an absolute humidity of the water vapor in the sample gas based on an intensity of the received infrared light of the specific wavelength. The density of the sample gas is determined by correcting for the influence of the water vapor included therein based on the absolute humidity in the sample gas detected by the humidity sensor.

1 Claim, 2 Drawing Sheets

INFRARED GAS DETECTOR AND METHOD OF THE SAME

CROSS REFERENCE TO RELATED APPLICATION

This application is based upon and claims the benefit of priority of Japanese Patent Application No. 2004-109379 filed on Apr. 1, 2004, the contents of which is incorporated herein by reference.

FIELD OF THE INVENTION

The present invention relates to an infrared gas detector having an infrared sensor, and, more specifically to an infrared gas detector having a correction function for water vapor interference.

BACKGROUND OF THE INVENTION

In recent years, infrared gas detectors have been developed for detection of gas density by sensing absorption of infrared light of specific wavelengths. For example, Japanese Patent Document JP-A-2003-50203 discloses an infrared gas detector having an infrared sensor for detecting absorption of infrared light.

The infrared gas detector (non-dispersive infrared gas detector) is equipped with multiple optical filters for filtering infrared light of specific wavelengths (passing infrared light of specific wavelengths). The filters are intended for filtering specific wavelength ranges of infrared light used to detect certain components of a sample gas. The infrared light is projected toward the gas in a sampling case, to be received by the infrared sensor after being filtered through the sample gas and the optical filters.

For example, water vapor density in a gas is affected by a carbon monoxide (CO) component. Therefore, when measuring a gas for water vapor density having CO, the CO interference in the measurement has to be corrected/removed by an optical filter in the infrared light path.

On the other hand, measuring a gas for CO density when water vapor is also present in the gas is performed in the following manner. The infrared light is filtered through an optical filter to introduce a wavelength range having a CO absorption rate and a relatively small water vapor absorption rate for the sample gas. Then, water vapor interference in the measurement is removed to have an accurate measurement of CO density. In this manner, density of a sample gas having infrared light absorption wavelength range similar to water vapor can be measured even in the presence of water vapor.

However, the optical filters have to be switched for a measurement of $H_2O$ and CO. In the disclosure described above, the $H_2O$ filter and the CO filter used for $H_2O$ measurement and CO measurement are disposed on a rotating chopper to cut the infrared light path alternately in a predetermined interval. In this case, the chopper is equipped with a position sensor to detect a filter position that is on the infrared light path at the moment, thereby making it difficult to enclose the infrared gas detector in a small package.

SUMMARY OF THE INVENTION

It is therefore an object of the present invention to provide an infrared gas detector that accurately detects density of a gas component having absorption wavelength range of infrared light similar to water vapor, and has a small package size. It is another object of the present invention to provide a method of gas detection for giving a correct measurement of gas density.

In order to achieve the above object, the infrared gas detector of the present invention measures the density of a sample gas by a detecting device for detecting absorption of infrared light of a specific wavelength range and outputting a signal proportional to the detected absorption amount, and a correctional function of infrared light absorption by water vapor component in the sample gas. The device may further comprise another detector for detecting absolute humidity for correction based on the absolute humidity.

The infrared gas detector of the present invention is capable of detecting absolute humidity. Therefore, the density of the sample gas is precisely detected by correcting for the interference of water vapor. The infrared gas detector of the present invention has another advantage in that it can be included in a small package because of the omission of plural optical filters, a chopper and a position sensor, even when a humidity detector is added.

The humidity detector may be a direct humidity detector or also an indirect humidity detector provided that it is capable of detecting absolute humidity of water vapor. For example, a relative humidity sensor or a due point meter together with a thermometer may be substituted for the direct humidity detector for absolute humidity detection.

Further, the infrared gas detector may be equipped with an infrared light emitting device that heats a resistive element to emit infrared light. The infrared light emitting device may be included in the infrared gas detector, or may be disposed separately from the detector.

The infrared gas detector may have a reference detector to output a reference signal by absorbing infrared light of a specific wavelength. The wavelength of infrared light for the reference is chosen to be different from the one absorbed by an object sample gas and from the one absorbed by the water vapor. The reference signal is used for correction of the measurement by the detector. In this manner, aging of an infrared light emitting device can be self-checked to prevent decreased sensitivity of the detector.

The reference detector may be disposed separately from the main part of the infrared gas detector, or may be disposed integrally in one package. When the reference detector is disposed in one package, accuracy of the reference detector benefits from being together with the main part of the detector in the same atmosphere. This results in a higher accuracy of the infrared gas detector because of an accurate reference signal, and a smaller package of the detector. The infrared gas detector may have the infrared light emitting device disposed either in the package or outside of the package.

BRIEF DESCRIPTION OF THE DRAWINGS

Other objects, features and advantages of the present invention will become more apparent from the following detailed description made with reference to the accompanying drawings, in which.

DETAILED DESCRIPTION OF THE PREFERRED EMBODIMENTS

Figure 1:
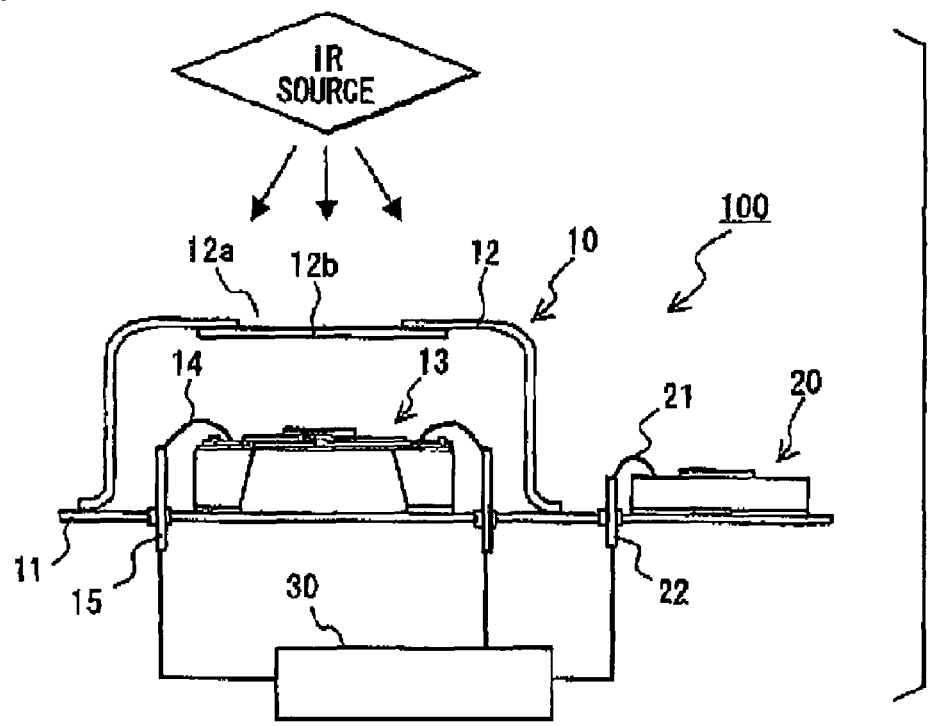
FIG. 1 is a schematic view of an infrared gas detector according to an embodiment of the present invention.

A schematic view of an infrared gas detector as an embodiment of the present invention is shown in FIG. 1. The infrared gas detector 100 comprises a detector 10 for detecting an infrared light of a specific wavelength, a humidity detector 20 for detecting absolute humidity of water vapor in a sample gas, and a processor 30 for processing signals from the detector 10 and the humidity detector 20.

The detector 10 includes a pedestal 11, a cap 12 disposed on the pedestal 11, and an infrared light sensor 13 disposed in a space defined by the pedestal 11 and the cap 12.

The cap 12 is used to limit incoming infrared light by the wavelength of infrared light and to an area on the infrared light sensor 13. Thus, the cap 12 prevents the infrared light from entering the space in the cap 12 except for a window 12a disposed on the cap 12. The window 12a allows the infrared light to be detected by the infrared light sensor 13. The window 12a has a band-pass filter 12b for selectively passing an infrared light of a specific wavelength that corresponds to an absorption wavelength range of the sample gas.

The infrared light sensor 13 is disposed on the pedestal 11 by using an adhesive, and outputs a signal proportional to the intensity of the infrared light of a specific wavelength received through the band-pass filter 12b to the processor 30. The infrared light sensor 13 in FIG. 1 is electrically connected to a terminal 15 perforatingly disposed on the pedestal 11 for external output through a bonding wire 14, as well as to the processor 30.

The infrared light sensor 13 may be a thermopile type sensor, a bolometer type sensor, a pyroelectric type sensor or the like. A thermopile type infrared sensor is used for the sensor 13 in this embodiment, which is formed by a general semiconductor process. A detailed description of the sensor 13 is disclosed in, for example, Japanese Patent Document JP-A-2002-365140, which has the same inventor as the present invention. The contents of Japanese Patent Document JP-A-2002-365140 are incorporated herein by reference.

The humidity detector 20 detects an absolute humidity of water vapor coexisting with the sample gas. The humidity detector 20 is disposed on the same surface of the pedestal 11 to which the infrared light sensor 13 is disposed. The absolute humidity of water vapor is, by definition, mass (a gram) of water vapor included in a unit volume (1 $m^3$).

The humidity detector 20 may detect the absolute humidity indirectly or may detect it directly. For example, a relative humidity sensor or a due point meter may be employed together with a thermometer for absolute humidity calculation. The humidity detector 20 in FIG. 1 is electrically connected to a terminal 22 perforatingly disposed on the pedestal 11 for external connection through a bonding wire 21, as well as to the processor 30.

The processor 30 calculates density of the sample gas by correcting for interference of water vapor included in the signal from the infrared sensor 13 in the detector 10 based on the signal from the humidity detector 20. Detailed explanation of removal of interference of water vapor is described later below.

Figure 2:
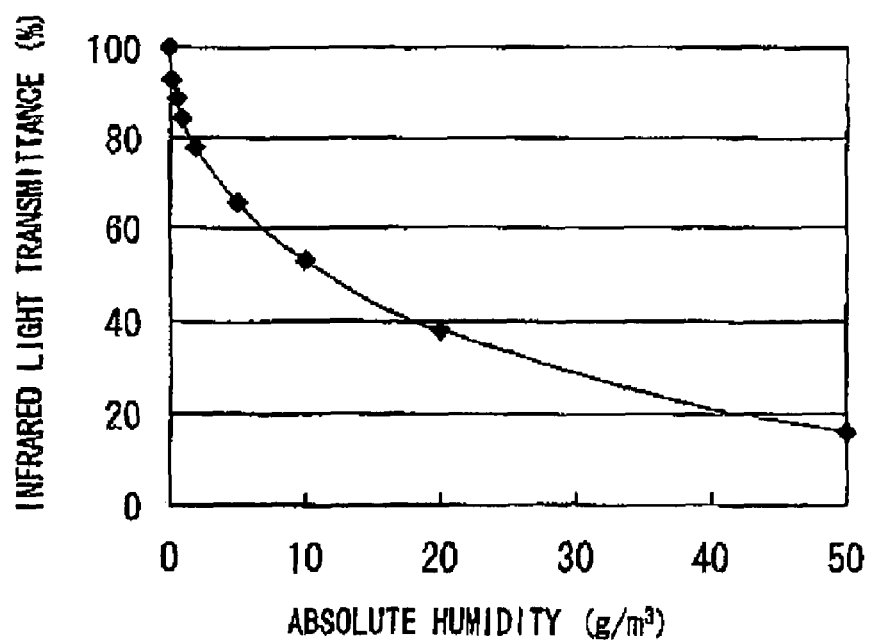
FIG. 2 is a diagram of a relationship between an absolute humidity and an infrared light transmittance.

The density detection method of the sample gas is explained with reference to FIGS. 2 and 3.

Density of the sample gas (for example, HFC-152a in this case) is generally detected with interference of water vapor when it is detected by using an infrared gas detector, because the infrared light of a specific wavelength absorbed by the gas is also absorbed at least partially by water vapor. That is, the density of the gas cannot be detected accurately as it is.

In the conventional approach for accurately detecting the gas density, first, an infrared light of a specific wavelength that is not absorbed by the sample gas is filtered by a qualitative optical filter, and the infrared light of the specific wavelength is used to measure the density of water vapor. Next, an infrared light of a different specific wavelength that is well absorbed by the sample gas but not so much absorbed by water vapor is filtered by another qualitative optical filter, and the infrared light of the different specific wavelength is introduced to measure the density of the sample gas under an interference of water vapor. Then, the interference of water vapor is removed to have an accurate measurement based on the water vapor density measured in the first step.

However, by using this method, two different kinds of optical filters (a filter for passing infrared light of specific wavelengths for water vapor density and another filter for the sample gas density) have to be used for the measurement, and the filters have to be placed and removed alternately in a specified interval in an infrared light path. Further, the positions of those filters have to be detected for determining which signal is being filtered by which filter. Therefore, in this case, the infrared gas detector tends to be large in terms of overall package size.

The infrared gas detector 100 in this embodiment uses the humidity sensor 20 to detect absolute humidity for removing interferenec of water vapor from the signal of the infrared light sensor 13. The relationship between the absolute humidity and infrared light transmittance of water vapor is shown, for example, in a diagram shown on pgs. 58-59 of the publication entitled "Infrared Light Engineering" written by Haruyoshi Hisano (1998), the conteuts of which are incorporated herein by reference. The diagram of the relationship is shown in FIG. 2. The wavelength of the infrared light used for the measurement of the diagram is 3.3 μm.

The absolute humidity of water vapor is, thus, detected based on the infrared light received by the humidity detector 20 as an infrared light transmittance. Then, the signal from the infrared light sensor 13 is corrected by removing interference of water vapor to have an accurate density of the sample gas, even when the infrared light of the specific wavelength is absorbed both by the sample gas and water vapor.

The gas density calculation method is described the following formula. In the formula, x represents infrared light transmittance (%) derived from absolute humidity, and y represents the signal detected by the infrared light sensor 13 under the influence of water vapor.

$$\text{Gas Density} = 100 y/x \qquad \text{(Formula)}$$

Figure 3:
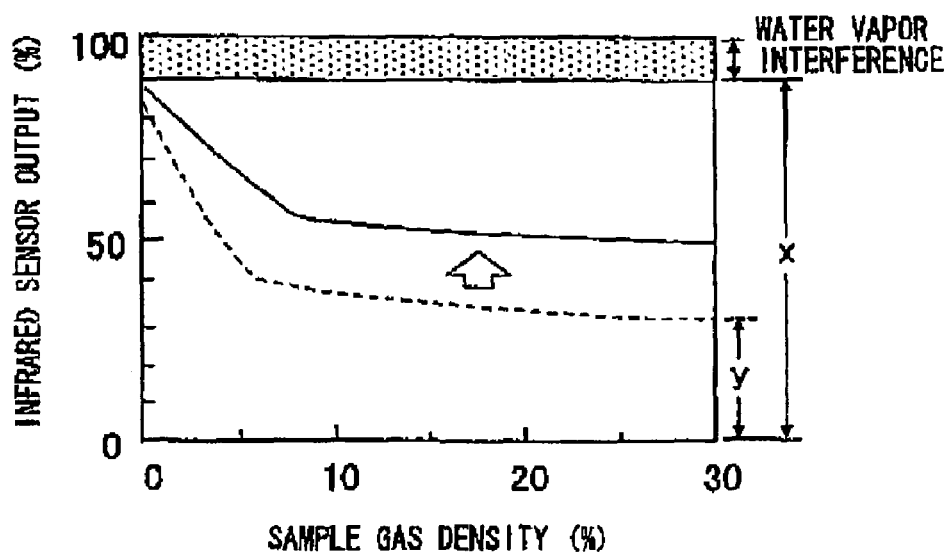
FIG. 3 is a diagram for an explanation of a relationship between a sample gas density, an infrared sensor output and water vapor interference.

The relationship shown in the above formula is depicted in FIG. 3. In FIG. 3, a hatching portion represents the interference of water vapor (100−x), a broken line represents an output signal y of the sensor 13 under the influence of water vapor, and a solid line represents a density of the sample gas after correction for water vapor interference.

In the present embodiment, a circuit chip in the processor 30 calculates an infrared light transmittance x by using the above formula based on the signal of absolute humidity from the humidity detector 20, and outputs the result of the calculation.

As the infrared gas detector 100 in this embodiment of the present invention can detect absolute humidity by the humidity detector 20, the detector 100 can correct for the interference of water vapor included in the signal from the infrared light sensor 13. That is, density of the sample gas can accurately be determined even when the infrared light of a specific wavelength is absorbed by both the sample gas and the water vapor.

The infrared gas detector 100 can be housed in a smaller package in comparison to conventional detectors because of the omission of the multiple qualitative optical filters, the chopper, and the position sensor even when the humidity detector 20 is added.

Those skilled in the art will appreciate that modifications may be made to the gas detector 100. For example, the circuit chips for signal processing may be both integrated in the infrared light sensor 13 and in the humidity detector 20, rather than being in the processor 30.

Further, although the signal from the infrared light sensor 13 (the detector 10) is corrected based on the absolute humidity detected by the humidity detector 20 in this embodiment, the infrared gas detector 100 may further include a reference detector to determine absorption of an infrared light of a specific wavelength that is neither absorbed by the sample gas nor water vapor, and to output a reference signal for correction.

Figure 4:
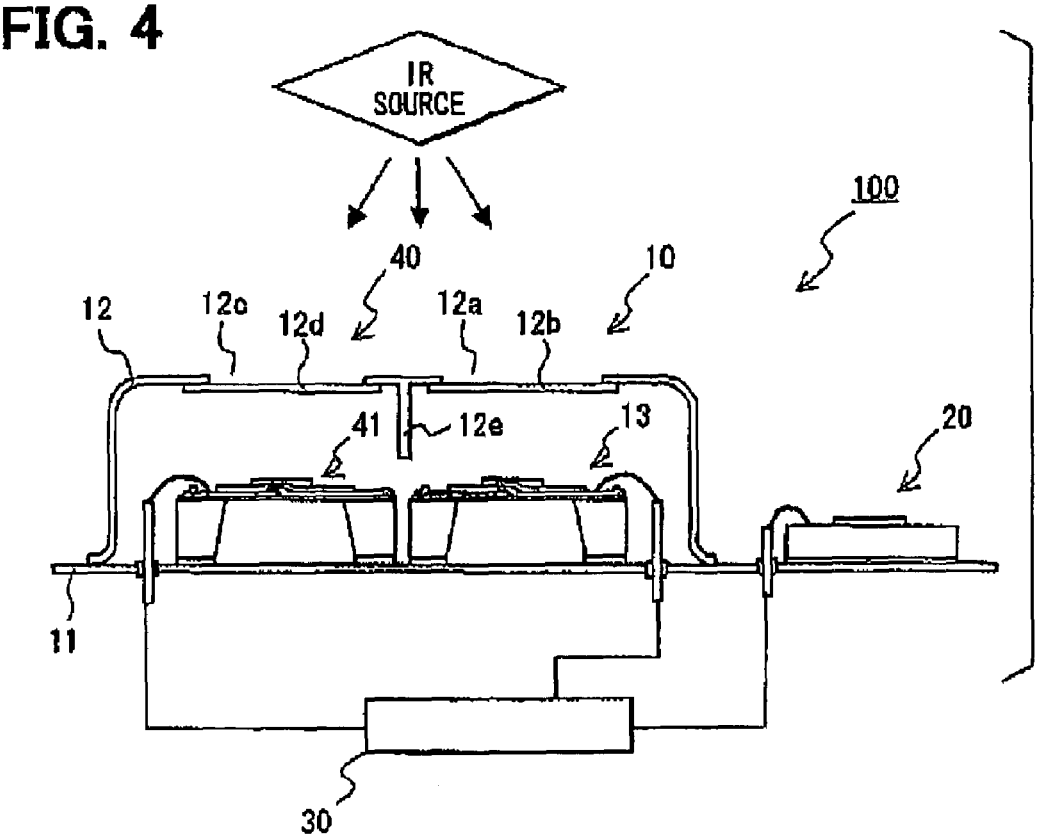
FIG. 4 is a schematic view of a modified embodiment of an infrared gas detector having a reference detector.

An infrared gas detector 100 with a reference detector is shown in FIG. 4. In FIG. 4, a reference detector 40 is integrally formed with the detector 10, and a reference infrared sensor 41 is disposed laterally with the infrared sensor 13 in the space defined by the cap 12 and the pedestal 11 of the detector 10. The reference infrared sensor 41 outputs a reference signal proportional to an infrared light received thereby. The cap 12 has a window 12c in a position opposed to the reference infrared sensor 41 for an incoming infrared light. The window 12c has a qualitative optical filter (a reference band-pass filter) 12d for selectively passing an infrared light of a specific wavelength that is neither absorbed by the sample gas nor water vapor. The cap 12 has a partition 12e extending downward from the cap 12 toward the pedestal 11 for separating infrared light incoming from the filter 12b to the infrared light sensor 13 and incoming from the filter 12d to the reference infrared light sensor 41. The reference infrared light sensor 41 is disposed on the pedestal 11 by using an adhesive, for example, and the sensor 41 exclusively captures the infrared light of a specific wavelength that passes through the filter 12d to output the reference signal corresponding to the intensity of the infrared light to the processor 30.

Therefore, the reference signal output from the reference detector 40 is affected neither by the sample gas nor water vapor. Thus, the reference signal from the reference detector 40 (an output from the reference infrared light sensor 41 based on the intensity of infrared light received thereby) is determined as a standard output, and is used for correction for aging of infrared light source with an index for light source aging. In this manner, decrease of the intensity of infrared light can be corrected to prevent the sensor from having decreased sensitivity.

Furthermore, an integrated structure of the reference detector 40 with the detector 10 in the cap 12 can effectively decrease positional dispersion of the sensors used in the infrared gas detector. The integrated structure also minimizes the difference of atmosphere (e.g., temperature) around the detector 10 and the detector 40, and thus benefits from a more accurate correction of the output signal based on the reference signal. Furthermore, the integrated structure enables the package of the infrared to be smaller. However, the reference detector 40 may be formed in a shape different from the one shown in FIG. 4. That is, the infrared sensor 13 and the reference infrared sensor 41 may be formed integrally on the same substrate, or may be formed separately in a different space defined by another cap 12 and another pedestal 11.

Further, the infrared gas detector may be equipped with an infrared light emitting device that heats a resistor to emit an infrared light. The infrared light emitting device may be included in the infrared gas detector, or may be disposed separately from the detector. The infrared gas detector 100 in the embodiment of the present invention is an example that has the light emitting device separately from a body of the infrared gas detector 100.

Further, the humidity detector 20 is disposed integrally on the same pedestal 11 as the infrared sensor 13 in the embodiment of the present invention. However, position of the humidity detector 20 is not limited to the one in the embodiment of the present invention.

Although the present invention has been fully described in connection with the preferred embodiments thereof with reference to the accompanying drawings, it is to be noted that various changes and modifications will become apparent to those skilled in the art. Such changes and modifications are to be understood as being within the scope of the present invention as defined by the appended claims.

What is claimed is:

1. An infrared gas detector for detecting a density of a sample gas comprising:
   a pedestal;
   a cap disposed on the pedestal, the cap including a window and a filter disposed in the window for selectively passing a specific wavelength of infrared light;
   an infrared light sensor disposed on the pedestal and within a cap, wherein the infrared light sensor is configured to output a first signal corresponding to a density of the sample gas under the influence of water vapor based upon based upon an intensity of the infrared light received at the infrared light sensor via the filter;
   a humidity sensor disposed on the pedestal and outside of the cap, the humidity sensor configured to output a second signal corresponding to an absolute humidity of the water vapor in the sample gas based on an intensity of infrared light received at the humidity sensor; and
   a processor configured to determine the density of the sample gas by correcting the detected density of the sample gas under the influence of water vapor based upon the detected absolute humidity.

* * * * *